United States Patent
Monk

(10) Patent No.: US 9,763,418 B1
(45) Date of Patent: Sep. 19, 2017

(54) SORGHUM HYBRID PHR4QYX

(71) Applicant: PIONEER HI-BRED INTERNATIONAL, INC., Johnston, IA (US)

(72) Inventor: Roger Monk, Fulshear, TX (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 15/345,620

(22) Filed: Nov. 8, 2016

(51) Int. Cl.
| | | |
|---|---|---|
| *A01H 5/10* | (2006.01) | |
| *C12N 15/82* | (2006.01) | |
| *A01H 1/02* | (2006.01) | |
| *C12Q 1/68* | (2006.01) | |

(52) U.S. Cl.
CPC .................. *A01H 5/10* (2013.01); *A01H 1/02* (2013.01); *C12Q 1/6895* (2013.01)

(58) Field of Classification Search
CPC ....................................................... A01H 5/10
USPC ......................................................... 800/320
See application file for complete search history.

(56) References Cited

U.S. PATENT DOCUMENTS

| | | | |
|---|---|---|---|
| 9,012,739 B1 * | 4/2015 | Monk | ................ C12N 15/8241 435/410 |
| 9,045,772 B1 | 6/2015 | Monk | |
| 2012/0073010 A1 * | 3/2012 | Bading | ..................... A23L 7/10 800/263 |

OTHER PUBLICATIONS

US Plant Variety Protection Certificate No. 201200209 for Sorghum Variety PHARSVXIT; issued Jan. 18, 2013.
US Plant Variety Protection Certificate No. 201100286 for Sorghum Variety PHAO8ZVKT; issued Aug. 18, 2011.

* cited by examiner

*Primary Examiner* — Li Zheng
(74) *Attorney, Agent, or Firm* — Pioneer Hi-Bred Int'l, Inc.

(57) ABSTRACT

A novel *sorghum* variety designated PHR4QYX and seed, plants, plant parts and plant cells thereof are produced from a cross of inbred *sorghum* varieties. Methods for producing a *sorghum* plant by crossing hybrid *sorghum* variety PHR4QYX with another *sorghum* plant and methods for producing a *sorghum* plant containing in its genetic material one or more traits introgressed into PHR4QYX through backcross conversion and/or transformation, and to the *sorghum* seed, plant and plant part produced thereby are described. *Sorghum* variety PHR4QYX, the seed, the plant produced from the seed, and variants, mutants, and minor modifications of *sorghum* variety PHR4QYX are provided.

19 Claims, No Drawings

SORGHUM HYBRID PHR4QYX

FIELD OF THE INVENTION

This invention relates generally to the field of plant breeding, specifically relating to hybrid grain *sorghum* variety designated PHR4QYX.

BACKGROUND OF THE INVENTION

One goal of plant breeding is to combine, in a single hybrid, various desirable traits. For field crops, these traits may include resistance to diseases and insects, resistance to heat and drought, reducing the time to crop maturity, greater yield, and better agronomic quality. Uniformity of plant characteristics such as germination and stand establishment, growth rate, maturity, plant height and fruit size facilitates mechanical harvesting. Traditional plant breeding through the development and use of inbred varieties facilitates the development of new and improved commercial crops.

SUMMARY OF THE INVENTION

According to the invention, there is provided a novel *sorghum*, *Sorghum bicolor* (L.) Moench), variety, seed, plant, and its parts designated as PHR4QYX, produced by crossing two Pioneer Hi-Bred International, Inc. proprietary *sorghum* inbred varieties. Discloses are the hybrid *sorghum* variety PHR4QYX the seed, the plant and its parts produced from the seed, and variants, mutants and minor modifications of *sorghum* PHR4QYX. Processes for making a *sorghum* plant containing in its genetic material one or more traits introgressed into PHR4QYX through locus conversion and/or transformation, and to the *sorghum* seed, plant and plant parts produced thereby are also provided. Further disclosed are methods for producing *sorghum* varieties derived from hybrid *sorghum* variety PHR4QYX.

Definitions

In the description and examples that follow, a number of terms are used herein. In order to provide a clear and consistent understanding of the specification and claims, including the scope to be given such terms, the following definitions are provided:

Anthracnose Resistance. This is a visual rating based on the number of lesions caused by anthracnose infection. A score of 9 would indicate little necrosis and a score of 1 would indicate plant death as a result of anthracnose infection.

Bacterial Spot. Bacterial Spot is a disease characterized by small, irregularly shaped lesions on the leaves. Bacterial Spot Resistance is rated on a scale of 1 to 9, with 1 being susceptible and 9 being resistant.

Bacterial Streak. Bacterial Streak is a disease characterized by narrow yellow stripes on the leaves. Bacterial Streak Resistance is rated on a scale of 1 to 9, with 1 being susceptible and 9 being resistant.

Bacterial Stripe. Bacterial Stripe is a disease characterized by long, narrow red stripes on the leaves. Bacterial Stripe Resistance is rated on a scale of 1 to 9, with 1 being susceptible and 9 being resistant.

Biotype C Greenbug Resistance. This is a visual rating based on the amount of necrosis on leaves and stems caused by biotype C greenbug feeding. A score of 9 would indicate no leaf or stem damage as a result of greenbug feeding.

Biotype E Greenbug Resistance. This is a visual rating based on plant seedlings ability to continue growing when infested with large numbers of biotype E greenbugs. A score of 9 indicates normal growth and a score of 1 indicates seedling death. Charcoal Rot. Charcoal Rot is a disease characterized by rotting of the roots and stalks. Charcoal Rot Resistance is rated on a scale of 1 to 9, with 1 being susceptible and 9 being resistant.

Chinch Bug Resistance. This is a visual rating based on the plants ability to grow normally when infested with large numbers of chinch bugs. A score of 9 would indicate normal growth and a score of 1 would indicate severe plant stunting and death.

Crop Response to Herbicide. Rated as the visual difference between sprayed and un-sprayed plants. A crop response of less than 30% means no visual difference, higher percentages means sprayed plants showed some damage.

Days to Flower. The days to flower is the number of days required for an inbred line or hybrid to shed pollen from the time of planting.

Days to Color. The days to color is the number of days required for an inbred line or hybrid to begin grain coloring from the time of planting. Coloring of the grain is correlated with physiological maturity, thus days to color gives an estimate of the period required before a hybrid is ready for harvest.

Days to Flower. The days to flower is the number of days required for an inbred line or hybrid to shed pollen from the time of planting.

Downy Mildew Resistance (Pathotypes 1 and 3). This is a visual rating based on the percentage of downy mildew infected plants. A score of 9 indicates no infected plants. A score of 1 would indicate higher than 50% infected plants. Ratings are made for infection by each pathotype of the disease.

Drought Tolerance. This represents a rating for drought tolerance and is based on data obtained under stress. It is based on such factors as yield, plant health, lodging resistance and stay green. A high score would indicate a hybrid tolerant to drought stress.

Dry Down. This represents the relative rate at which a hybrid will reach acceptable harvest moisture compared to other hybrids. A high score indicates a hybrid that dries relatively fast while a low score indicates a hybrid that dries slowly.

*Fusarium* Root and Stalk Rot. *Fusarium* Root and Stalk Rot is a disease characterized by rotting of the roots and stalks. *Fusarium* Root and Stalk Rot Resistance is rated on a scale of 1 to 9, with 1 being susceptible and 9 being resistant.

Grain Mold. Grain Mold is characterized by the formation of mold on heads and grain. Grain Mold Resistance is rated on a scale of 1 to 9, with 1 being susceptible and 9 being resistant.

Gray Leaf Spot Resistance. This is a visual rating based on the number of gray leaf spot lesions present on the leaves and stem of the *sorghum* plant. A score of 9 would indicate the presence of few lesions.

Head Exertion. This represents a rating for the length of the peduncle exposed between the base of the panicle (head) and the flag leaf of the plant. A high score indicates more distance between the flag leaf and the *sorghum* head while a low score indicates a short distance between the two. Head exertion facilitates ease of combine harvesting.

Head Smut Resistance (Races 1-4). This is a visual rating based on the percentage of smut infected plants. A score of 9 would indicate no infected plants and a score of 1 would indicate higher than 50% infected plants. Ratings are made for each race of head smut.

Head Type. This represents a rating of the morphology of the *sorghum* panicle (head). A high score indicates an open panicle caused by either more distance between panicle branches or longer panicle branches. A low score indicates a more compact panicle caused by shorter panicle branches arranged more closely on the central rachis.

Leaf Burn Resistance. This is a visual rating based on the amount of tissue damage caused by exposure to insecticide sprays. A score of 9 would indicate minor leaf spotting and a score of 1 would indicate leaf death as a result of contact with insecticide spray.

Locus Conversion (Also called a Trait Conversion): A locus conversion refers to a modified plant within a variety that retains the overall genetics of the variety and further includes a locus with one or more specific desired traits, and otherwise has the same, essentially the same, all or essentially all of the physiological and morphological characteristics of the variety, such as listed in Table 1. Traits can be directed to, for example, modified grain, male sterility, insect control, disease control or herbicide tolerance. Traits can be mutant genes, transgenic sequences or native traits. A single locus conversion refers to plants within a variety that have been modified in a manner that retains the overall genetics of the variety and include a single locus with one or more specific desired traits. A single locus conversion can include at least or about 1, 2, 3, 4 or 5 traits and less than or about 15, 10, 9, 8, 7 or 6 traits. A locus converted plant can include, for example, at least or about 1, 2 or 3 and less than or about 20, 15, 10, 9, 8, 7, 6, or 5 modified loci while still retaining the overall genetics of the variety and otherwise having essentially the same, the same, all or essentially all of the physiological and morphological characteristics of the variety, such as listed in Table 1. The total number of traits at one or more locus conversions can be, for example, at least or about 1, 2, 3, 4 or 5 and less than or about 25, 20, 15, 10, 9, 8, 7 or 6. Examples of single locus conversions include mutant genes, transgenes and native traits finely mapped to a single locus. Traits may be introduced by transformation, backcrossing, or a combination of both.

Maize Dwarf Mosaic Virus Resistance. This is a visual rating based on the percentage of plants showing symptoms of virus infection. A score of 9 would indicate no plants with virus symptoms and a 1 would indicate a high percentage of plants showing symptoms of virus infection such as stunting, red leaf symptoms or leaf mottling.

Midge Resistance. This is a visual rating based on the percentage of seed set in the panicle in the presence of large numbers of midge adults. A score of 9 would indicate near normal seed set and a score of 1 would indicate no seed set in the head due to midge damage.

Moisture. The moisture is the actual percentage moisture of the grain at harvest.

Plant: As used herein, the term "plant" includes reference to an immature or mature whole plant, including a plant from which seed or grain has been removed.

Plant Height. This is a measure of the average height of the hybrid from the ground to the tip of the panicle and is measured in inches.

Plant Part: As used herein, the term "plant part" includes leaves, stems, roots, seed, grain, kernels, panicles, embryo, pollen, ovules, flowers, stalks, root tips, anthers, pericarp, protoplasts, tissue, plant calli, cells and the like. In some embodiments the plant part contains at least one cell of hybrid *sorghum* variety PHR4QYX.

Percent Yield. The percent yield is the yield obtained from the hybrid in terms of percent of the mean for the experiment in which it was grown.

Predicted RM. This trait, predicted relative maturity (RM), for a hybrid is based on the number of days required for an inbred line or hybrid to shed pollen from the time of planting. The relative maturity rating is based on a known set of checks and utilizes standard linear regression analyses.

*Puccinia* (Rust) Resistance. This is a visual rating based on the number of rust pustules present on the leaves and stem of the plant. A score of 9 would indicate the presence of few rust pustules.

RM to Color. This trait for a hybrid is based on the number of days required for a hybrid to begin to show color development in the grain from the time of planting. The relative maturity rating is based on a known set of checks and utilizes standard linear regression analyses.

Root Lodging. This represents a rating of the percentage of plants that do not root lodge, i.e. those that lean from the vertical axis at an approximate 30 degree angle or greater without stalk breakage are considered to be root lodged. This is a relative rating of a hybrid to other hybrids for standability. Root lodging is rated on a scale of 1 to 9, with 1 indicating greater than 50% lodged plants and 9 indicating no lodged plants.

Sales Appearance. This represents a rating of the acceptability of the hybrid in the market place. It is a complex score including such factors as hybrid uniformity, appearance of yield, grain texture, grain color and general plant health. A high score indicates the hybrid would be readily accepted based on appearance only. A low score indicates hybrid acceptability to be marginal based on appearance only.

Salt Tolerance. This represents a rating of the plants ability to grow normally in soils having high sodium salt content. This is a relative rating of a hybrid to other hybrids for normal growth.

Selection Index. The selection index gives a single measure of the hybrid's worth based on information for up to five traits. A *sorghum* breeder may utilize his or her own set of traits for the selection index. Two of the traits that are almost always included are yield and days to flower (maturity). The selection index data presented in the tables in the specification represent the mean values averaged across testing stations.

Stalk Lodging. This represents a rating of the percentage of plants that do not stalk lodge, i.e. stalk breakage above the ground caused by natural causes. This is a relative rating of a hybrid to other hybrids for standability. Stalk lodging is rated on a scale of 1 to 9, with 1 indicating greater than 50% lodged plants and 9 indicating no lodged plants.

Stay Green. Stay green is the measure of plant health near the time of harvest. A high score indicates better late-season plant health.

Test Weight. This is the measure of the weight of the grain in pounds for a given volume (bushel) adjusted for percent moisture.

Weathering. This represents a rating of how well the exposed grains are able to retain normal seed quality when exposed to normal weather hazards and surface grain molds.

Yield (cwt/acre). The yield in cwt/acre is the actual yield of the grain at harvest adjusted to 13% moisture.

Yield/RM. This represents a rating of a hybrid yield compared to other hybrids of similar maturity or RM. A high score would indicate a hybrid with higher yield than other hybrids of the same maturity.

Yield Under Stress. This is a rating of the plants ability to produce grain under heat and drought stress conditions. A score of 9 would indicate near normal growth and grain yield and a score of 1 would indicate substantial yield reduction due to stress.

Zonate Leaf Spot Resistance. This is a visual rating based on the number of zonate leaf spot lesions present on the leaves and stem of the *sorghum* plant. A score of 9 would indicate the presence of few lesions.

DETAILED DESCRIPTION OF THE INVENTION

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous plants from differing backgrounds or two homozygous lines produce a uniform population of hybrid plants that may be heterozygous for many gene loci. A cross of two plants that are each heterozygous at a number of gene loci will produce a population of hybrid plants that differ genetically and will not be uniform.

*Sorghum* plants (*Sorghum bicolor* L. Moench) are bred in most cases by self-pollination techniques. With the incorporation of male sterility (either genetic or cytoplasmic) cross pollination breeding techniques can also be utilized. *Sorghum* has a perfect flower with both male and female parts in the same flower located in the panicle. The flowers are usually in pairs on the panicle branches. Natural pollination occurs in *sorghum* when anthers (male flowers) open and pollen falls onto receptive stigma (female flowers). Because of the close proximity of male (anthers) and female (stigma) in the panicle, self-pollination is very high (average 94%). Cross pollination may occur when wind or convection currents move pollen from the anthers of one plant to receptive stigma on another plant. Cross pollination is greatly enhanced with incorporation of male sterility which renders male flowers nonviable without affecting the female flowers. Successful pollination in the case of male sterile flowers requires cross pollination.

*Sorghum* is in the same family as maize and has a similar growth habit, but with more tillers and a more extensively branched root system. *Sorghum* is more drought resistant and heat-tolerant than maize. It requires an average temperature of at least 25° C. to produce maximum yields. *Sorghum*'s ability to thrive with less water than maize may be due to its ability to hold water in its foliage better than maize. *Sorghum* has a waxy coating on its leaves and stems which helps to keep water in the plant even in intense heat. Wild species of *sorghum* tend to grow to a height of 1.5 to 2 meters; however in order to improve harvestability, dwarfing genes have been selected in cultivated varieties and hybrids such that most cultivated varieties and hybrids grow to between 60 and 120 cm tall.

Hybrid Development

The development of *sorghum* hybrids requires the development of homozygous inbred lines, the crossing of these lines, and the evaluation of the crosses. Pedigree breeding methods, and to a lesser extent population breeding methods, are used to develop inbred lines from breeding populations. Breeding programs combine desirable traits from two or more inbred lines into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced. $F_1$ to $F_2$; $F_2$ to $F_3$; $F_3$ to $F_4$, $F_4$ to $F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate genes(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

*Sorghum* varieties are mainly self-pollinated; therefore, self-pollination of the parental varieties must be controlled to make hybrid development feasible. A pollination control system and effective transfer of pollen from one parent to the other offers improved plant breeding and an effective method for producing hybrid seed and plants. For example, the milo or $A_1$ cytoplasmic male sterility (CMS) system, developed via a cross between milo and kafir cultivars, is one of the most frequently used CMS systems in hybrid *sorghum* production (Stephens J C & Holland P F, *Cytoplasmic Male Sterility for Hybrid Sorghum Seed Production*, Agron. J. 46:20-23 (1954)). Other CMS systems for *sorghum* include, but are not limited to, $A_2$, isolated from IS 12662c (Schertz K F, *Registration of $A_2T_x$ 2753 and $BT_x$ 2753 Sorghum Germplasm*, Crop Sci. 17: 983 (1977)), $A_3$, isolated from IS 1112c or converted Nilwa (Quinby J R, *Interactions of Genes and Cytoplasms in Male-Sterility in Sorghums*, Proc. 35th Corn *Sorghum* Res. Conf. Am. Seed Trade Assoc. Chicago, III., pp. 5-8 (1980)), $A_4$, isolated from IS 7920c (Worstell et al, *Relationship among Male-Sterility Inducing Cytoplasms of Sorghum*, Crop Sci. 24:186-189 (1984)).

In developing improved new *sorghum* hybrid varieties, breeders may use a CMS plant as the female parent. In using these plants, breeders attempt to improve the efficiency of seed production and the quality of the $F_1$ hybrids and to reduce the breeding costs. When hybridization is conducted without using CMS plants, it is more difficult to obtain and isolate the desired traits in the progeny ($F_1$ generation) because the parents are capable of undergoing both cross-pollination and self-pollination. If one of the parents is a CMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of $F_1$ hybrids includes crossing a CMS female parent with a pollen-producing male parent. To reproduce effectively, however, the male parent of the $F_1$ hybrid must have a fertility restorer gene (Rf gene). The presence of an Rf gene means that the $F_1$ generation will not be completely or partially sterile, so that either self-pollination or cross pollination may occur. Self-pollination of the $F_1$ generation to produce several subsequent generations is important to ensure that a desired trait is heritable and stable and that a new variety has been isolated.

Promising advanced breeding lines commonly are tested and compared to appropriate standards in environments representative of the commercial target area(s). The best lines are candidates for new commercial lines; and those still deficient in a few traits may be used as parents to produce new populations for further selection.

A hybrid sorghum variety is the cross of two inbred lines. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid sorghum variety involves five steps: (1) the formation of "restorer" and "non-restorer" germplasm pools; (2) the selection of superior plants from various "restorer" and "non-restorer" germplasm pools; (3) the selfing of the superior plants for several generations to produce a series of inbred lines, which although different from each other, each breed true and are highly uniform; (4) the conversion of inbred lines classified as non-restorers to cytoplasmic male sterile (CMS) forms, and (5) crossing the selected cytoplasmic male sterile (CMS) inbred lines with selected fertile inbred lines (restorer lines) to produce the hybrid progeny ($F_1$).

Because sorghum is normally a self-pollinated plant and because both male and female flowers are in the same panicle, large numbers of hybrid seed can only be produced by using cytoplasmic male sterile (CMS) inbreds. Flowers of the CMS inbred are fertilized with pollen from a male fertile inbred carrying genes which restore male fertility in the hybrid ($F_1$) plants. An important consequence of the homozygosity and homogeneity of the inbred lines is that the hybrid between any two inbreds will always be the same. Once the inbreds that produce the best hybrid have been identified, the hybrid seed can be reproduced indefinitely as long as the homogeneity of the inbred parent is maintained.

A single cross hybrid is produced when two inbred lines are crossed to produce the $F_1$ progeny. Much of the hybrid vigor exhibited by $F_1$ hybrids is lost in the next generation ($F_2$). Consequently, seed from hybrid varieties is not used for planting stock.

Hybrid grain sorghum can be produced using wind to move the pollen. Alternating strips of the cytoplasmic male sterile inbred (female) and the male fertile inbred (male) are planted in the same field. Wind moves the pollen shed by the male inbred to receptive stigma on the female. Providing that there is sufficient isolation from sources of foreign sorghum pollen, the stigma of the male sterile inbred (female) will be fertilized only with pollen from the male fertile inbred (male). The resulting seed, born on the male sterile (female) plants is therefore hybrid and will form hybrid plants that have full fertility restored.

Locus Conversions of Sorghum Line PHR4QYX

PHR4QYX represents a new base genetic line into which a new locus or trait may be introduced. Direct transformation and backcrossing represent two important methods that can be used to accomplish such an introgression. The term locus conversion is used to designate the product of such an introgression.

To select and develop a superior hybrid, it is necessary to identify and select genetically unique individuals that occur in a segregating population. The segregating population is the result of a combination of crossover events plus the independent assortment of specific combinations of alleles at many gene loci that results in specific and unique genotypes. Once such a variety is developed its value to society is substantial since it is important to advance the germplasm base as a whole in order to maintain or improve traits such as yield, disease resistance, pest resistance and plant performance in extreme weather conditions. Locus conversions are routinely used to add or modify one or a few traits of such a line and this further enhances its value and usefulness to society.

Backcrossing can be used to improve inbred varieties and a hybrid variety which is made using those inbreds. Backcrossing can be used to transfer a specific desirable trait from one variety, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent.

Traits may be used by those of ordinary skill in the art to characterize progeny. Traits are commonly evaluated at a significance level, such as a 1%, 5% or 10% significance level, when measured in plants grown in the same environmental conditions. For example, a locus conversion of PHR4QYX may be characterized as having essentially the same phenotypic traits as PHR4QYX. The traits used for comparison may be those traits shown in Table 1. Molecular markers can also be used during the breeding process for the selection of qualitative traits. For example, markers can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants.

A locus conversion of PHR4QYX will retain the genetic integrity of PHR4QYX. For example, a locus conversion of PHR4QYX can be developed when DNA sequences are introduced through backcrossing (Hallauer et al., 1988), with a parent of PHR4QYX utilized as the recurrent parent. Both naturally occurring and transgenic DNA sequences may be introduced through backcrossing techniques. A backcross conversion may produce a plant with a locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses. A locus conversion of PHR4QYX can be determined through the use of a molecular profile. A locus conversion of PHR4QYX would have 92%, 93%, 94%, 95%, 96%, 97%, 98% or 99% of the molecular markers, or molecular profile, of PHR4QYX. Examples of molecular markers that could be used to determine the molecular profile include Restriction Fragment Length Polymorphisms (RFLP), Polymerase Chain Reaction (PCR) analysis, and Simple Sequence Repeats (SSR), and Single Nucleotide Polymorphisms (SNPs).

Transformation of *Sorghum* Line PHR4QYX

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes."

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick. In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson, Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular *sorghum* plant using transformation techniques, could be moved into another line using traditional breeding techniques that are well known in the plant breeding arts. For example, a backcrossing approach could be used to move a transgene from a transformed *sorghum* plant to an elite inbred line and the resulting progeny would comprise a transgene. Also, if an inbred line was used for the transformation then the transgenic plants could be crossed to a different line in order to produce a transgenic hybrid *sorghum* plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. For example, see, U.S. Pat. No. 6,118,055.

With transgenic plants according to the present discovery, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, (1981) Anal. Biochem. 114:92-96.

A genetic map can be generated, primarily via conventional Restriction Fragment Length Polymorphisms (RFLP), Polymerase Chain Reaction (PCR) analysis, and Simple Sequence Repeats (SSR), and Single Nucleotide Polymorphisms (SNPs), which identifies the approximate chromosomal location of the integrated DNA molecule coding for the foreign protein. For exemplary methodologies in this regard, see, Glick and Thompson, METHODS IN PLANT MOLECULAR BIOLOGY AND BIOTECHNOLOGY 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNP, and sequencing, all of which are conventional techniques.

Likewise, by means of the present discovery, plants can be genetically engineered to express various phenotypes of agronomic interest. Exemplary transgenes implicated in this regard include, but are not limited to, those categorized below.

1. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) "Site-Specific Recombination for Genetic Engineering in Plants", Plant Cell Rep 21:925-932 and WO 99/25821, which are hereby incorporated by reference. Other systems that may be used include the Gin recombinase of phage Mu (Maeser, et al., 1991), the Pin recombinase of *E. coli* (Enomoto, et al., 1983), and the R/RS system of the pSR1 plasmid (Araki, et al., 1992).

2. Genes that affect abiotic stress resistance (including but not limited to flowering, panicle/glume and seed development, enhancement of nitrogen utilization efficiency, altered nitrogen responsiveness, drought resistance or tolerance, cold resistance or tolerance, and salt resistance or tolerance) and increased yield under stress.

For example, see, WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521 and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. Nos. 10/817,483 and 09/545,334 where cytokinin expression is modified resulting in plants with increased stress tolerance, such as drought tolerance, and/or increased yield. Also see WO0202776, WO03052063, JP2002281975, U.S. Pat. No.

6,084,153, WO0164898, U.S. Pat. No. 6,177,275 and U.S. Pat. No. 6,107,547 (enhancement of nitrogen utilization and altered nitrogen responsiveness). For ethylene alteration, see, US Patent Application Publication Numbers 2004/0128719, 2003/0166197 and WO200032761. For plant transcription factors or transcriptional regulators of abiotic stress, see e.g., US Patent Application Publication Number 2004/0098764 or US Patent Application Publication Number 2004/0078852.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), and WO2004076638 and WO2004031349 (transcription factors).

3. Transgenes that Confer or Contribute to an Altered Grain Characteristic, Such as:
  A. Altered phosphorus content, for example, by the
    (1) Introduction of a phytase-encoding gene would enhance breakdown of phytate, adding more free phosphate to the transformed plant. For example, see, Van Hartingsveldt, et al., Gene 127:87 (1993), for a disclosure of the nucleotide sequence of an *Aspergillus niger* phytase gene.
    (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al. (1990).
  B. Altered fatty acids, for example, by down-regulation of stearoyl-ACP desaturase to increase stearic acid content of the plant. See Knultzon, et al., Proc. Natl. Acad. Sci. USA 89:2624 (1992).
  C. Altered carbohydrates effected, for example, by altering a gene for an enzyme that affects the branching pattern of starch, a gene altering thioredoxin. (See, U.S. Pat. No. 6,531,648). See, Shiroza, et al., (1988) J. Bacteriol 170:810 (nucleotide sequence of *Streptococcus mutans* fructosyltransferase gene), Steinmetz, et al., (1985) Mol. Gen. Genet. 200:220 (nucleotide sequence of *Bacillus subtilis* levansucrase gene), Pen, et al., (1992) Bio/Technology 10:292 (production of transgenic plants that express *Bacillus licheniformis* alpha-amylase), Elliot, et al., (1993) Plant Molec Biol 21:515 (nucleotide sequences of tomato invertase genes), Segaard, et al., (1993) J. Biol. Chem. 268:22480 (site-directed mutagenesis of barley alpha-amylase gene) and Fisher, et al., (1993) Plant Physiol 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.
  D. Altered antioxidant content or composition, such as alteration of tocopherol or tocotrienols. For example, see, U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt).
  E. Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP).

4. Genes that Confer Male Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on," the promoter, which in turn allows the gene that confers male fertility to be transcribed.
  A. A dominant nuclear gene, Ms(tc) controlling male sterility. See, Elkonin, L. A., Theor. Appl. Genet. (2005) 111(7): 1377-1384.
  B. A tapetum-specific gene, RTS, a *sorghum* anther-specific gene is required for male fertility and its promoter sequence directs tissue-specific gene expression in different plant species. Luo, Hong, et al., Plant Molecular Biology., 62(3): 397-408(12) (2006). Introduction of a deacetylase gene under the control of a tapetum-specific promoter and with the application of the chemical N—Ac—PPT. See International Publication No. WO 01/29237.

C. Introduction of various stamen-specific promoters. Anther-specific promoters which are of particular utility in the production of transgenic male-sterile monocots and plants for restoring their fertility. See, U.S. Pat. No. 5,639,948. See also, International Publication Nos. WO 92/13956 and WO 92/13957.

D. Introduction of the barnase and the barstar genes. See, Paul, et al., Plant Mol. Biol., 19:611-622 (1992).

For additional examples of nuclear male and female sterility systems and genes, see also, U.S. Pat. Nos. 5,859,341, 6,297,426, 5,478,369, 5,824,524, 5,850,014, and 6,265,640. See also, Hanson, Maureen R., et al., "Interactions of Mitochondrial and Nuclear Genes That Affect Male Gametophyte Development," Plant Cell., 16:S154-S169 (2004), all of which are hereby incorporated by reference.

A. Modification of RNA editing within mitochondrial open reading frames. See, Pring, D. R., et al, Curr. Genet. (1998) 33(6): 429-436; Pring, D. R., et al., J. Hered. (1999) 90(3): 386-393; Pring, D. R., et al., Curr. Genet. (2001) 39(5-6): 371-376; and Hedgcoth, C., et al., Curr. Genet. (2002) 41(5): 357-365.

B. Cytoplasmic male sterility (CMS) from mutations at atp6 codons. See, Kempken, F., FEBS. Lett. (1998): 441(2): 159-160.

C. Inducing male sterility through heat shock. See, Wang, L., Yi Chuan Xue Bao. (2000) 27(9): 834-838.

D. Inducing male sterility through treatment of streptomycin on *sorghum* callus cultures. See, Elkonin, L. A., et al., Genetica (2008) 44(5): 663-673.

Uses of *Sorghum*

*Sorghum* is used as livestock feed, as sugar or grain for human consumption, as biomass, and as raw material in industry. *Sorghum* grain can be used as livestock feed, such as to beef cattle, dairy cattle, hogs and poultry. In some embodiments, the plant is used as livestock feed in the form of fodder, silage, hay and pasture. In some embodiments, commodity plant products produced from hybrid seed such as food, feed, forage, and syrup are provided.

Provided are uses of *sorghum* in the form of bread, porridge, confectionaries and as an alcoholic beverage. Grain *sorghum* may be ground into flour and either used directly or blended with wheat or corn flour in the preparation of food products. In addition to direct consumption of the grain, *sorghum* has long been used in many areas of the world to make beer. The uses of *sorghum*, in addition to human consumption of kernels, include both products of dry and wet milling industries. The principal products of *sorghum* dry milling are grits, meal and flour. Starch and other extracts for food use can be provided by the wet milling process.

Also provided are uses of *sorghum* as an industrial raw material. Industrial uses include *sorghum* starch from the wet-milling industry and *sorghum* flour from the dry milling industry. *Sorghum* starch and flour have application in the paper and textile industries. Other industrial uses include applications in adhesives, building materials and as oil-well muds. Considerable amounts of *sorghum*, both grain and plant material, have been used in industrial alcohol production.

Characteristics of PHR4QYX

Hybrid *sorghum* line PHR4QYX, a grain *sorghum* hybrid, was developed by Pioneer Hi-Bred International, Inc. *Sorghum* line PHR4QYX has all, or essentially all, the phenotypic characteristics shown in Table 1. Provided are seed of *sorghum* line PHR4QYX, plants of *sorghum* line PHR4QYX, plant parts of *sorghum* line PHR4QYX, and plant cells of *sorghum* line PHR4QYX.

Hybrid *sorghum* line PHR4QYX can be made by crossing inbreds PHAO8ZVKT and PHARSVXIT. Locus conversions of hybrid *sorghum* variety PHR4QYX can be made by crossing inbreds PHAO8ZVKT and PHARSVXIT wherein one or both of PHAO8ZVKT and PHARSVXIT comprise a locus conversion(s). Hybrid *sorghum* line PHR4QYX has shown uniformity and stability within the limits of environmental influence for all, or essentially all, of the phenotypic traits such as described in the Variety Description Information (Table 1).

Hybrid *sorghum* line PHR4QYX can be advantageously used in accordance with the breeding methods described herein and those known in the art to produce other hybrids and progeny plants retaining desired trait combinations of hybrid *sorghum* line PHR4QYX. Provided are methods for producing a *sorghum* plant by crossing a first parent *sorghum* plant with a second parent *sorghum* plant wherein either the first or second parent *sorghum* plant is hybrid *sorghum* line PHR4QYX. Further, both first and second parent *sorghum* plants can come from the hybrid *sorghum* line PHR4QYX. Either the first or the second parent plant may be male sterile. Processes for making a plant may comprise crossing *sorghum* line PHR4QYX with another plant.

The terms variants, modification and mutant refer to a hybrid seed or a plant produced by that hybrid seed which is phenotypically similar to PHR4QYX.

The foregoing discovery has been described in detail by way of illustration and example for purposes of exemplification. However, it will be apparent that changes and modifications such as single gene modifications and mutations, somaclonal variants, variant individuals selected from populations of the plants of the instant variety, and the like, are considered to be within the scope of the present discovery. All references disclosed herein whether to journal, patents, published applications and the like are hereby incorporated in their entirety by reference.

DEPOSITS

Applicant has made or will make a deposit of at least 2,500 seeds of parental *sorghum* inbred varieties PHAO8ZVKT and PHARSVXIT with the American Type Culture Collection (ATCC), 10801 University Boulevard, Manassas, Va. 20110-2209, USA, with ATCC Deposit Nos. PTA-122099 and PTA-121965, respectively. The seeds deposited with the ATCC on Apr. 17, 2015 for PTA-122099 and on Jan. 29, 2015 for PTA-121965, were obtained from the seed of the variety maintained by Pioneer Hi-Bred International, Inc., 7250 NW 62nd Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. These deposits of the seed of parental *sorghum* inbred varieties for *Sorghum* Variety PHR4QYX will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of the rights granted under this patent or rights applicable to *Sorghum* Variety PHR4QYX and/or its parental *sorghum* inbred varieties PHAO8ZVKT and PHARSVXIT under either the patent laws or the Plant Variety Protection Act (7 USC 2321 et seq.). Unauthorized seed multiplication is prohibited.

TABLE 1

Variety Descriptions based on Morphological, Agronomic and Quality Traits

| Trait | Category | Description |
|---|---|---|
| Kind | 1 | Sorghum |
| 1 = Sorghum | | |
| 2 = Sorghum x Almum | | |
| 3 = Sudangrass | | |
| 4 = Johnsongrass | | |
| 5 = Other | | |
| Male Sterile Cytoplasm | 1 | A-1 |
| 1 = A-1 | | |
| 2 = A-2 | | |
| 3 = A-3 | | |
| 4 = A-4 | | |
| 5 = A-5 | | |
| 6 = Other | | |
| Use Class: | 1 | Grain |
| 1 = Grain | | |
| 2 = Forage | | |
| 3 = Silage | | |
| 4 = Sugar | | |
| 5 = Syrup | | |
| 6 = Broomcorn | | |
| 7 = Multipurpose | | |
| Days from planting to mid-anthesis | | |
| Plant Coleptile | 1 | Green |
| 1 = Green | | |
| 2 = Red | | |
| Plant pigment | 3 | Purple |
| 1 = Tan | | |
| 2 = Red | | |
| 3 = Purple | | |
| 4 = Other: Specify | | |
| Plant height in inches | | 46 |
| Plant: Natural height of foliage at panicle emergence | 5 | Medium |
| 1 = Very short | | |
| 3 = Short | | |
| 5 = Medium | | |
| 7 = High | | |
| 9 = Very high | | |
| Plant: Total height at maturity | 5 | Medium |
| 1 = Very short | | |
| 3 = Short | | |
| 5 = Medium | | |
| 7 = High | | |
| 9 = Very high | | |
| Diameter of main stalk | 2 | Mid stout |
| 1 = Slim | | |
| 2 = Mid stout | | |
| 3 = Stout | | |
| Stalk Height (cm from soil to top of panicle) | | 117 |
| Waxy Bloom | 1 | Present |
| 1 = Present | | |
| 2 = Absent | | |

TABLE 1-continued

Variety Descriptions based on Morphological, Agronomic and Quality Traits

| Trait | Category | Description |
|---|---|---|
| Number of Tillers | 2 | Moderate |
| 1 = Few | | |
| 2 = Moderate | | |
| 3 = Many | | |
| Stem Sweetness | 2 | Insipid |
| 1 = Sweet | | |
| 2 = Insipid | | |
| Stem Juiciness | 1 | Dry (Pithy) |
| 1 = Dry (Pithy) | | |
| 2 = Juicy | | |
| Panicle Exsertion | 2 | Medium |
| 1 = Short | | |
| 2 = Medium | | |
| 3 = Long | | |
| Degree of Senescence | 3 | Intermediate |
| 1 = Senescent | | |
| 2 = Nonsenescent | | |
| 3 = Intermediate | | |
| Stem: Stem diameter one third of height of plant at maturity | 5 | Medium |
| 3 = Small | | |
| 5 = Medium | | |
| 7 = Large | | |
| Stem Thickness | | Mid stout |
| Slender | | |
| Mid stout | | |
| Stout | | |
| Leaf width (relative to class) | 3 | Wide |
| 1 = Narrow | | |
| 2 = Moderate | | |
| 3 = Wide | | |
| Leaf Color | 1 | Light Green |
| 1 = Light Green | | |
| 2 = Dark Green | | |
| Leaf margin | 2 | Wavy |
| 1 = Smooth | | |
| 2 = Wavy | | |
| Leaf attitude or erectness | 1 | Erect |
| 1 = Erect | | |
| 2 = Horizontal | | |
| 3 = Drooping | | |
| Ligule | 1 | Present |
| 1 = Present | | |
| 2 = Absent | | |
| Leaf midrib color | 1 | White |
| 1 = White | | |
| 2 = Intermediate | | |
| 3 = Cloudy | | |
| 4 = Yellow | | |
| 5 = Brown | | |
| Leaf: Length of blade of the third leaf from top at maturity | 7 | Long |
| 1 = Very Short | | |
| 3 = Short | | |
| 5 = Medium | | |
| 7 = Long | | |
| 9 = Very Long | | |
| Leaf: Width of blade of the third leaf from top at maturity | 7 | Broad |
| 1 = Very narrow | | |
| 3 = Narrow | | |
| 5 = Medium | | |
| 7 = Broad | | |
| 9 = Very broad | | |
| Number of leaves originating from nodes above ground | | 10 |
| Panicle Anther Color (at flowering) | 2 | Light Yellow |
| 1 = White | | |
| 2 = Light Yellow | | |
| 3 = Dark Yellow | | |
| 4 = Wine | | |

TABLE 1-continued

Variety Descriptions based on Morphological, Agronomic and Quality Traits

| Trait | Category | Description |
|---|---|---|
| Panicle Length (cm) | | 33 |
| Panicle: Length of branches in the middle third of the panicle | 5 | Medium |
| 3 = Short | | |
| 5 = Medium | | |
| 9 = Long | | |
| Panicle Density | 3 | Semi-Compact |
| 1 = Open | | |
| 2 = Semi-Open | | |
| 3 = Semi-Compact | | |
| 4 = Compact | | |
| Panicle Shape at maturity | 3 | Symmetric |
| 1 = Reversed pyramide | | |
| 2 = Panicle broader at upper part | | |
| 3 = Symmetric | | |
| 4 = Panicle braoder in lower part | | |
| 5 = Pyramidal | | |
| Panicle erectness | | Erect |
| Panicle Type | 3 | More cylindrical sorghum panicle type |
| 1 = Very open like sudangreas | | |
| 2 = large and bushy | | |
| 3 = More cylindrical sorghum panicle type | | |
| 4 = Broader at the bottom, pointed at the top of the panicle | | |
| 5 = Very compact, short panicle length, club head | | |
| 6 = Round goosenick type panicle | | |
| 7 = Short central rachis, long rachis branches growing horizontal or drooping | | |
| Neck of panicle: Visible length above sheath or flag leaf at maturity | 5 | Medium |
| 1 = Absent or very short | | |
| 3 = Short | | |
| 5 = Medium | | |
| 7 = Long | | |
| 9 = Very long | | |
| Panicle Density | 3 | Semi-Compact |
| 1 = Open | | |
| 2 = Semi-Open | | |
| 3 = Semi-Compact | | |
| 4 = Compact | | |
| Panicle: Length without neck at maturity | 5 | Medium |
| 1 = Very short | | |
| 3 = Short | | |
| 5 = Medium | | |
| 7 = Long | | |
| 9 = Very long | | |
| Length of central rachis (% of panicle length) | 2 | 75% |
| 1 = 100% | | |
| 2 = 75% | | |
| 3 = 50% | | |
| 4 = 25% | | |
| Rachis branches at grain maturity | 1 | Erect |
| 1 = Erect | | |
| 2 = Horizontal | | |
| 3 = Drooping | | |
| Rachis Branch Average | 2 | Intermediate |
| 1 = Short | | |
| 2 = Intermediate | | |
| 3 = Long | | |
| Rachis branches | | Heavily fruited |
| Heads break at maturity | | Few break |
| Rachis | | % of head = 85 Rachis length = 11 inches Length of branches = 2.5 inches |
| Glume length at maturity | 1 | Short |
| 1 = Short | | |
| 2 = Intermediate | | |
| 3 = Long | | |
| Percent of grain covered by the glume | 1 | 25% |
| 1 = 25% | | |
| 2 = 50% | | |
| 3 = 75% | | |
| 4 = 100% | | |
| 5 = Over 100% | | |
| Glume Texture | 2 | Intermediate |
| 1 = Papery | | |
| 2 = Intermediate | | |
| 3 = Leathery | | |
| Glume color at grain maturity | 1 | Black |
| 1 = Black | | |
| 2 = Mahogany | | |
| 3 = Red | | |
| 4 = Sienna | | |
| 5 = Dark Tan | | |
| 6 = Light Tan | | |
| Glume Hairiness or pubescence | 1 | Smooth |
| 1 = Smooth | | |
| 2 = Intermediate | | |
| 3 = Hairy | | |
| Glume Veination | 2 | Absent |
| 1 = Present | | |
| 2 = Absent | | |
| Glume Transverse Wrinkle | 2 | Absent |
| 1 = Present | | |
| 2 = Absent | | |
| Glume Awns | 1 | Absent |
| 1 = Absent | | |
| 2 = Short | | |
| 3 = Intermediate | | |
| 4 = Long | | |
| Glume Apices | | Acute |
| Acute | | |
| Rounded | | |
| Obtuse | | |
| Roots | 1 | Fibrous |
| 1 = Fibrous | | |
| 2 = Rhizomatous | | |
| Grain Testa | 1 | Absent |
| 1 = Absent | | |
| 2 = Present | | |
| Grain Mesocarp Thickness | 1 | Thin |
| 1 = Thin | | |
| 2 = Intermediate | | |
| 3 = Thick | | |
| Grain Epicarp Color (Genetic) | 3 | Red |
| 1 = White | | |
| 2 = Lemon Yellow | | |
| 3 = Red | | |
| Grain Spreader (Tannin in Pericarp) | 1 | Absent |
| 1 = Absent | | |
| 2 = Present | | |
| Grain Intensifier | 1 | Absent |
| 1 = Absent | | |
| 2 = Present | | |
| Grain Color (Appearance) | 5 | Light Red |
| 1 = White Pearly | | |
| 2 = White Chalky (Opaque) | | |
| 3 = Yellow | | |
| 4 = Lemon Yellow | | |
| 5 = Light Red | | |
| 6 = Dark Red | | |
| 7 = Light Brown | | |
| 8 = Reddish Brown | | |
| 9 = Dark Brown | | |
| 10 = Purple | | |
| 11 = Other | | |
| Grain Endosperm Color | 2 | Yellow |
| 1 = White | | |
| 2 = Yellow | | |

TABLE 1-continued

Variety Descriptions based on
Morphological, Agronomic and Quality Traits

| Trait | Category | Description |
|---|---|---|
| Grain Endosperm Type | 1 | Starchy |
| 1 = Starchy | | |
| 2 = Waxy | | |
| 3 = Sugary | | |
| Grain Endosperm Texture | 2 | Intermediate |
| 1 = Floury | | |
| 2 = Intermediate | | |
| 3 = Corneous | | |
| Grain Seed Shape | 1 | Round |
| 1 = Round | | |
| 2 = Oval | | |
| 3 = Ovate | | |
| 4 = Turtleback | | |
| No. of seed per 100 G Genotype | | 3500 |

What is claimed is:

1. An F1 hybrid *sorghum* variety PHR4QYX seed, wherein representative seed of the variety is produced by crossing a first plant of variety PHAO8ZVKT with a second plant of variety PHARSVXIT, and wherein representative seed of the varieties PHAO8ZVKT and PHARSVXIT have been deposited under ATCC Accession Numbers PTA-122099 and PTA-121965, respectively.

2. The F1 hybrid *sorghum* variety PHR4QYX seed of claim 1, wherein a seed treatment has been applied to the seed.

3. A method comprising cleaning the F1 hybrid *sorghum* variety PHR4QYX seed of claim 1.

4. An F1 plant, plant part, or plant cell produced by growing the F1 hybrid *sorghum* variety PHR4QYX seed of claim 1, wherein the plant part comprises at least one cell of F1 hybrid *sorghum* variety PHR4QYX.

5. The F1 plant, plant part, or plant cell of claim 4, wherein the plant, plant part or plant cell is a pollen or ovule.

6. A method of making a commodity plant product, the method comprising growing the plant of claim 4 and producing the commodity plant product from grain or plant material harvested therefrom.

7. A method for producing a second *sorghum* plant, the method comprising applying plant breeding techniques to the plant or plant part of claim 4 to produce the second *sorghum* plant.

8. A method comprising:
 (a) crossing the plant or plant part of claim 4 with itself or a different plant to produce progeny seed;
 (b) growing the progeny seed to produce a progeny plant and crossing the progeny plant with itself or a different plant to produce further progeny seed; and
 (c) repeating step (b) for at least an additional two generations to produce a second *sorghum* plant.

9. A method comprising generating a molecular marker profile from nucleic acids isolated from the hybrid *sorghum* variety PHR4QYX seed of claim 1.

10. A converted seed of F1 hybrid *sorghum* variety PHR4QYX, wherein the converted seed is produced by crossing a first plant of variety PHAO8ZVKT with a second plant of variety PHARSVXIT; wherein representative seed of the varieties PHAO8ZVKT and PHARSVXIT have been deposited under ATCC Accession Numbers PTA-122099 and PTA-121965, respectively; and wherein at least one of the varieties PHAO8ZVKT and PHARSVXIT further comprises a locus conversion and wherein the converted seed produces a plant which otherwise has essentially the same morphological and physiological characteristics as *sorghum* variety PHR4QYX when grown under the same environmental conditions.

11. The converted seed of claim 10, wherein a seed treatment has been applied to the converted seed.

12. A method comprising cleaning the converted seed of claim 10.

13. The converted seed of claim 10, wherein the locus conversion confers a property selected from the group consisting of male sterility, site-specific recombination, abiotic stress tolerance, altered phosphorus, altered antioxidants, altered fatty acids, altered essential amino acids, altered carbohydrates, herbicide tolerance, insect resistance and disease resistance.

14. A method comprising generating a molecular marker profile from nucleic acids isolated from the hybrid *sorghum* variety PHR4QYX seed of claim 10.

15. A plant, plant part, or plant cell produced by growing the converted seed of claim 10, wherein the plant part comprises at least one cell of the converted F1 hybrid *sorghum* variety PHR4QYX.

16. The F1 plant, plant part, or plant cell of claim 15, wherein the plant, plant part or plant cell is a pollen or ovule.

17. A method of making a commodity plant product comprising producing the commodity plant product from the plant or plant part of claim 15.

18. A method for producing a second *sorghum* plant, the method comprising applying plant breeding techniques to the plant or plant part of claim 15 to produce the second *sorghum* plant.

19. A method comprising:
 (a) crossing the plant or plant part of claim 15 with itself or a different plant to produce progeny seed;
 (b) growing the progeny seed to produce a progeny plant and crossing the progeny plant with itself or a different plant to produce further progeny seed; and
 (c) repeating step (b) for at least an additional two generations to produce a second *sorghum* plant.

\* \* \* \* \*